(12) United States Patent
Shusterman (10) Patent No.: US 11,020,601 B2
(45) Date of Patent: Jun. 1, 2021

(54) ACCESSORY FOR EXTERNAL CARDIAC DEFIBRILLATION, PACING AND MONITORING PHYSIOLOGICAL SIGNALS/HEALTH DATA IN THE PRESENCE OF ELECTROMAGNETIC INTERFERENCE

(71) Applicant: Vladimir Shusterman, Pittsburgh, PA (US)

(72) Inventor: Vladimir Shusterman, Pittsburgh, PA (US)

(*) Notice: Subject to any disclaimer, the term of this patent is extended or adjusted under 35 U.S.C. 154(b) by 54 days.

(21) Appl. No.: 15/963,095

(22) Filed: Apr. 25, 2018

(65) Prior Publication Data

US 2018/0243574 A1 Aug. 30, 2018

Related U.S. Application Data

(63) Continuation-in-part of application No. 15/442,705, filed on Feb. 27, 2017, now Pat. No. 10,842,440, (Continued)

(51) Int. Cl.
*A61B 5/0205* (2006.01)
*A61N 1/39* (2006.01)
(Continued)

(52) U.S. Cl.
CPC ............ *A61N 1/3904* (2017.08); *A61B 5/002* (2013.01); *A61B 5/0006* (2013.01); *A61B 5/0024* (2013.01); *A61B 5/0205* (2013.01); *A61B 5/318* (2021.01); *A61B 5/7203* (2013.01); *A61B 5/7217* (2013.01); *A61B 5/7221* (2013.01); *A61B 5/7225* (2013.01); *A61N 1/3625* (2013.01); *A61N 1/36139* (2013.01);
(Continued)

(58) Field of Classification Search
None
See application file for complete search history.

(56) References Cited

U.S. PATENT DOCUMENTS

5,730,146 A * 3/1998 Itil .................. A61B 5/0476
600/545
6,221,011 B1 * 4/2001 Bardy .................. G06F 19/324
600/300
(Continued)

*Primary Examiner* — Sunit Pandya (57) ABSTRACT

This accessory adapts external cardiac defibrillation systems to enable safe defibrillation, pacing, and cardioversion inside the MRI bore with minimal effect on MR image quality. Commercially available external defibrillators are not designed to work in the MRI environment. An MR-compatible defibrillator is needed to safely perform cardiovascular MRI, in particular MR-guided interventional cardiovascular procedures, such as cardiac electrophysiology studies and cardiac catheterization. This accessory includes nonmagnetic defibrillator housing with MRI safety features, provides interface for MRI-compatible physiological monitoring, and optimizes defibrillator operation for the MRI environment. The accessory may include MRI-compatible modules for monitoring/recording electrocardiogram, blood pressure, pulse oximetry, and other physiological signals. It may also include a wireless transmitter and at least one module for electrical energy generation and/or stimulation.

20 Claims, 5 Drawing Sheets

Related U.S. Application Data which is a continuation-in-part of application No. 14/470,923, filed on Aug. 27, 2014, now Pat. No. 9,610,016.

(60) Provisional application No. 62/622,996, filed on Jan. 29, 2018, provisional application No. 62/490,031, filed on Apr. 26, 2017.

(51) Int. Cl.
| | | |
|---|---|---|
| *A61B 5/00* | (2006.01) | |
| *A61N 1/36* | (2006.01) | |
| *A61N 1/362* | (2006.01) | |
| *A61N 1/37* | (2006.01) | |
| *A61B 5/318* | (2021.01) | |
| *G08C 17/02* | (2006.01) | |
| *A61B 5/021* | (2006.01) | |
| *A61B 5/055* | (2006.01) | |
| *A61B 5/053* | (2021.01) | |
| *A61B 5/1455* | (2006.01) | |
| *A61B 5/026* | (2006.01) | |
| *A61B 5/369* | (2021.01) | |
| *A61B 5/389* | (2021.01) | |

(52) U.S. Cl.
CPC ......... *A61N 1/3718* (2013.01); *A61N 1/3931* (2013.01); *G08C 17/02* (2013.01); *A61B 5/021* (2013.01); *A61B 5/0263* (2013.01); *A61B 5/053* (2013.01); *A61B 5/055* (2013.01); *A61B 5/14551* (2013.01); *A61B 5/369* (2021.01); *A61B 5/389* (2021.01); *A61B 5/7282* (2013.01); *A61N 1/36031* (2017.08); *A61N 1/3993* (2013.01)

(56) References Cited

U.S. PATENT DOCUMENTS

| | | | | |
|---|---|---|---|---|
| 6,753,783 | B2 * | 6/2004 | Friedman | A61B 5/0002 |
| | | | | 324/207.11 |
| 7,508,307 | B2 * | 3/2009 | Albert | G08B 1/08 |
| | | | | 340/506 |
| 8,137,270 | B2 * | 3/2012 | Keenan | A61B 5/0456 |
| | | | | 600/301 |
| 8,388,530 | B2 * | 3/2013 | Shusterman | G16H 50/20 |
| | | | | 600/300 |
| 8,437,843 | B1 * | 5/2013 | Kayyali | A61B 5/0024 |
| | | | | 600/544 |
| 8,781,563 | B2 * | 7/2014 | Foo | A61B 5/1117 |
| | | | | 600/509 |
| 9,183,351 | B2 * | 11/2015 | Shusterman | G06F 19/3418 |
| 2005/0165323 | A1 * | 7/2005 | Montgomery | A61B 5/0476 |
| | | | | 600/544 |
| 2006/0183980 | A1 * | 8/2006 | Yang | G16H 20/30 |
| | | | | 600/301 |
| 2007/0010721 | A1 * | 1/2007 | Chen | G06Q 50/22 |
| | | | | 600/300 |
| 2007/0288265 | A1 * | 12/2007 | Quinian | G16H 40/67 |
| | | | | 705/2 |
| 2011/0004110 | A1 * | 1/2011 | Shusterman | G16H 50/20 |
| | | | | 600/509 |
| 2013/0172691 | A1 * | 7/2013 | Tran | A61B 5/026 |
| | | | | 600/301 |
| 2013/0231947 | A1 * | 9/2013 | Shusterman | A61B 5/0452 |
| | | | | 705/2 |
| 2014/0081100 | A1 * | 3/2014 | Muhsin | A61B 5/7203 |
| | | | | 600/324 |
| 2014/0213872 | A1 * | 7/2014 | Rahman | A61B 5/02438 |
| | | | | 600/372 |
| 2014/0266776 | A1 * | 9/2014 | Miller | A61B 5/0015 |
| | | | | 340/870.01 |
| 2015/0106020 | A1 * | 4/2015 | Chung | G16H 40/67 |
| | | | | 702/19 |

* cited by examiner

ACCESSORY FOR EXTERNAL CARDIAC DEFIBRILLATION, PACING AND MONITORING PHYSIOLOGICAL SIGNALS/HEALTH DATA IN THE PRESENCE OF ELECTROMAGNETIC INTERFERENCE

STATEMENT REGARDING FEDERALLY SPONSORED RESEARCH OR DEVELOPMENT

This invention was made with government support under contract HHSN268201500009C awarded by the National Institutes of Health. The government has certain rights in the invention.

FIELD OF THE INVENTION

This invention relates to the field of biomedical methods and systems for external defibrillation, pacing, and cardioversion in the presence of strong electromagnetic interference (EMI) and electromagnetic forces (EMF) generated by magnetic resonance imaging (MRI) scanners.

BACKGROUND OF THE INVENTION

This application is a continuation-in-part of pending U.S. patent application Ser. No. 15/442,705 filed on Feb. 27, 2017, which is a continuation-in-part of U.S. patent application Ser. No. 14/470,923 filed on Aug. 27, 2014 (now U.S. Pat. No. 9,610,016), which are incorporated herein in their entirety by reference. This application also claims the benefit of U.S. Provisional Application No. 62/490,031, filed Apr. 26, 2017, and U.S. Provisional Application No. 62/622,996, filed Jan. 29, 2018, which are incorporated herein by reference.

Interventional cardiovascular MRI (IC-MRI) allows physicians to perform minimally invasive and catheter-based diagnostic procedures, such as cardiac catheterization and electrophysiology (EP) studies, providing high-quality images of internal organs without exposure to harmful ionizing radiation. Because interventional cardiology procedures (in particular EP studies) often involve arrhythmia induction and termination, an absence of in-bore defibrillation and pacing impedes the development of IC-MRI. Therefore, there is a need for a system that can provide cardiac monitoring, defibrillation, and pacing, as well as patient mobility, because many procedures (e.g., right-heart catheterization using real-time MR guidance) are typically performed under combined MRI and X-ray guidance, necessitating rapid patient transport between the MRI and X-ray rooms.

Modern hospital-grade defibrillators also provide vital-sign monitoring (including electrocardiogram [ECG], blood pressure, and pulse oximetry) for diagnosing arrhythmias and optimizing the timing of defibrillation discharges and pacing with respect to the patient's cardiac cycle. Therefore, there is also a need for an external defibrillation and pacing system that can function during the extreme EMI and EMF generated by MRI scanners during the procedures.

SUMMARY OF THE INVENTION

Figure 1:
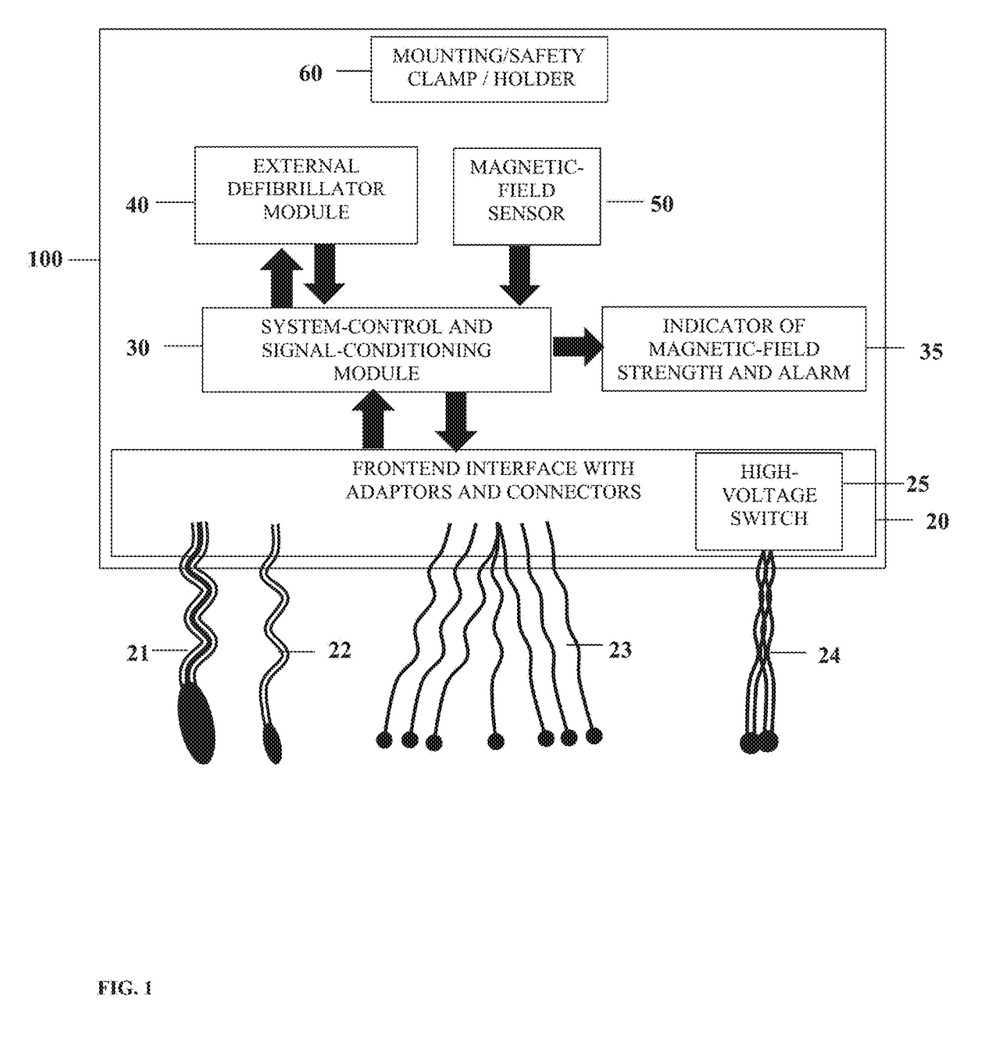
FIG. 1 is a block diagram of an embodiment of the MAGNA-DEX system architecture that includes a nonmagnetic enclosure (100) and a frontend interface (20), which provides connectors, adaptors and switches for connecting the input cables (e.g., ECG cables [23], blood-pressure cable(s) [22], and pulse-oximetry cable [21] from an MRI-compatible hemodynamic monitoring system); the output cables (e.g., defibrillation cables [24]); and (optional) filters for the input and output signals transmitted through the cables described above. The frontend interface (20) also includes a high-voltage switch (25) for selecting an operational regime/mode that provides optimal system performance with minimal EMI (see Description of Preferred Embodiments for details). The system architecture also includes the system-control and signal-conditioning module (30), an indicator of the magnetic-field strength and associated audio-visual alarm (35) when the magnetic field strength exceeds a preset threshold, a defibrillator module (40), a magnetic-field sensor (50), and a mounting/safety tool, e.g., a clamp and/or holder (60) which allows mounting/securing the system on a stable, nonmagnetic object.

A block diagram of the system of this invention is shown in FIG. 1. We note that the terms unit and module are used interchangeably throughout this document. Furthermore, the terms subject and patient herein are also used interchangeably to denote a living being, to whom the system of this invention is being applied. The terms nonmagnetic, substantially nonmagnetic, nonferromagnetic, and weakly magnetic herein are used interchangeably to denote materials that are not strongly attracted by magnetic fields.

This invention describes an MRI-enabling accessory (magnetic resonance imaging accessory for defibrillation, external; MAGNA-DEX), which adapts any commercially available external defibrillator for safe operation in the MRI environment, using the following three sets of features (which herein are also interchangeably referred to as the blocks, units, modules, elements):

I. One or more safety features selected from:
  A. An enclosure, which is adapted for housing an external defibrillator and which may further include a mounting tool (clamp and/or holder) that secures MAGNA-DEX in place (despite the attraction force generated by the MRI magnet) by mounting (or attaching) the system to a stable, secure object (e.g., a nonmagnetic pole attached to a patient table, wall, ceiling, or floor). The enclosure is made from a nonmagnetic material, such as bronze, brass, zinc, or plastic. The enclosure may be designed to provide incomplete or partial coverage of the defibrillator, e.g., a frontend enclosure, a rear enclosure, or an enclosure covering three sides of the defibrillator.
  B. A magnetic-field sensor, for example, a sensor based on the Hall effect, with an associated indicator of high (e.g., >200 Gauss) magnetic-field strength and/or an audio and/or visual alarm activated when the magnetic-field strength exceeds a preset threshold; the alarm may include an LED indicator and/or audio alarm (buzzer).

II. A frontend interface panel containing connectors and adaptors to enable interfacing/connecting one or more connectors selected from:
  A. the defibrillator's input connectors with:
    i. the cables transmitting physiological monitoring signals, e.g., ECG, blood pressure, pulse oximetry, directly from an individual (with or without filtering electromagnetic interference and/or other types of noise), or
    ii. the cables transmitting physiological monitoring signals from an MRI-compatible monitoring system (e.g., the PELEX-MAX hemodynamic monitoring system, PinMed, Inc., Pittsburgh, Pa., which provides 12-lead ECG, blood pressure signals from fluid-filled catheters or from noninvasive [cuff-based or cuff-free] blood-pressure measurements, pulse-oximetry waveform, and SpO2 signals), and
  B. the defibrillator's output connectors, which may include the defibrillator's output-mode-selection switch (described below) and the associated connector for the output defibrillation cable with defibrillation pads/electrodes (e.g., disposable; radiolucent Quik-Combo electrodes/pads, Physio-Control, Redmond, Wash.).

The defibrillator output-mode-selection switch enables the selection of an optimal operational regime that minimizes the impact of defibrillator-generated EMI on the MR image quality. In particular, the switch provides the following operational regimes (modes):
  A. An "EMI-free" operating mode regime, in which the defibrillator's current is redirected to an internal circuit/resistor located in module (30), thereby discontinuing the current injection into the defibrillation cables and electrodes, thus providing EMI-free operation. This mode is useful during diagnostic (high-quality) MR imaging.

B. A "defibrillation" mode, in which the defibrillator's current is directed to the defibrillation cables and electrodes, thus enabling: 1) accurate estimation of the electrical impedance of the contact between the patient's skin and the defibrillator's electrodes/pads, and 2) subsequent defibrillation. This mode is useful, e.g., during a test/procedure which does not require high-quality diagnostic MR imaging but may require external defibrillation, e.g., during MR-guided cardiovascular interventions, stress test, or MR-guided EP procedures.

C. "Advanced, custom" regimes that provide automatic switching between modes #1 and #2 above to combine the benefits of both modes and to minimize EMI. For example, mode switching can be performed:
1. At constant time intervals (e.g., once/minute);
2. At time intervals that are tailored to the subject's heart rate (e.g., once in 10 heartbeats);
3. At time intervals tailored to the subject's breathing (e.g., once in every $2^{nd}$ breathing cycle);
4. Custom time intervals selected by a user;
5. Other operational regimes which optimize the defibrillator's operation for application specifics and minimize the EMI impact on MR images, including the regimes optimized for synchronous (on-demand) pacing with inhibition of pacing during intrinsic cardiac activity, asynchronous pacing, and cardioversion, which involves delivery of electrical discharges at specific time points synchronized with intrinsic cardiac activity.

Figure 2:
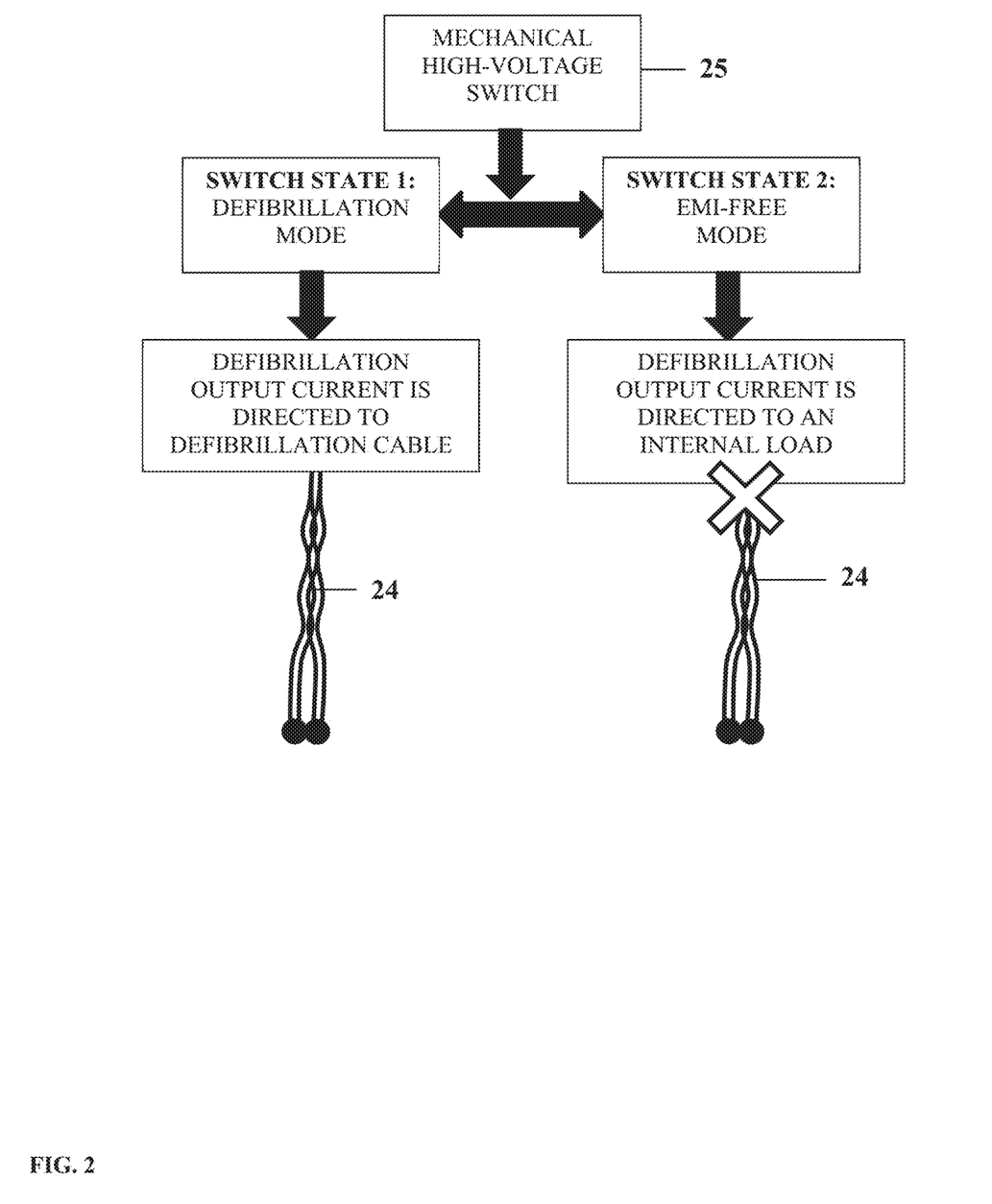
Figure 3:
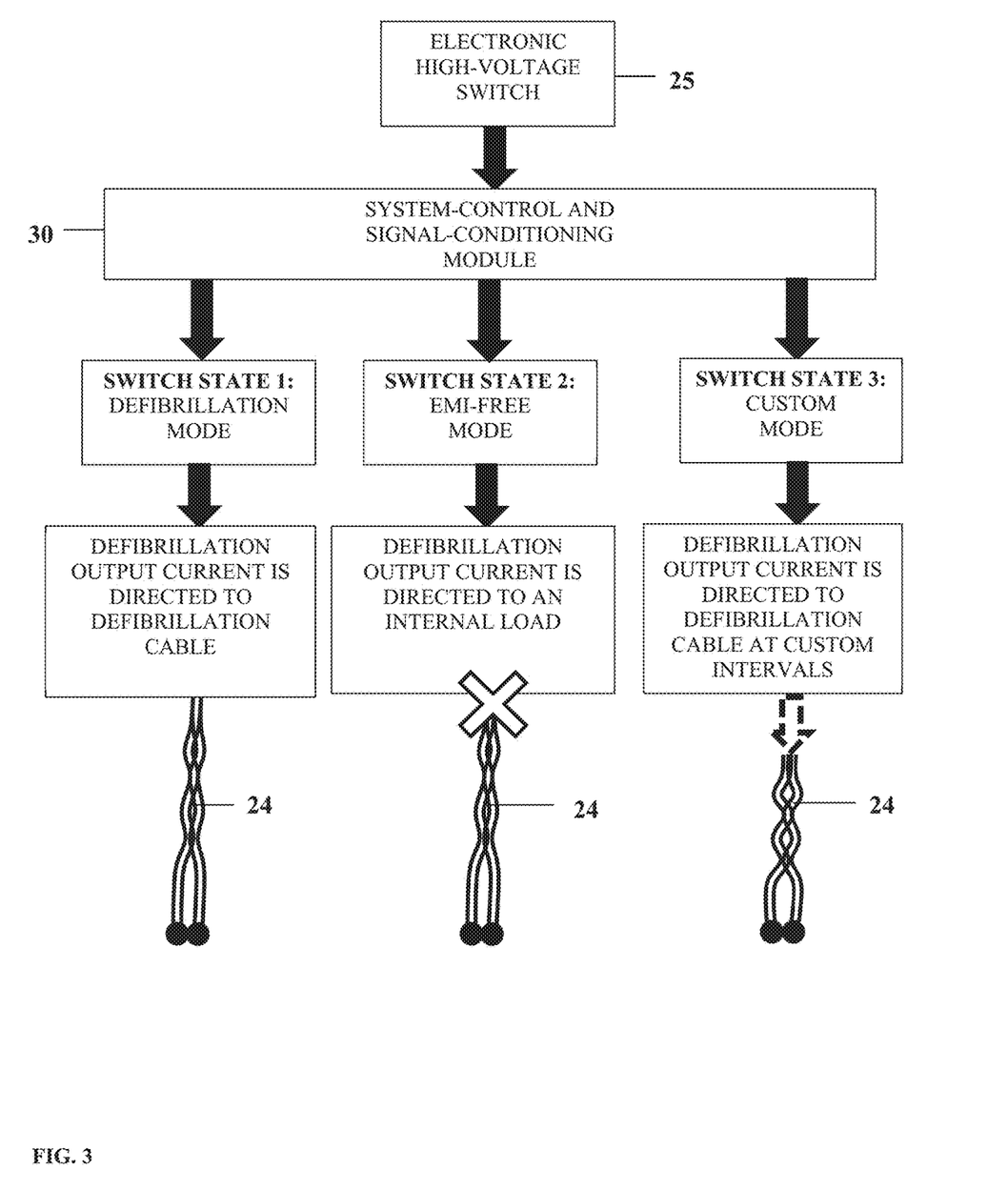

The switch is implemented using either mechanical components (FIG. 2, mechanical switch) or electronic components (FIG. 3, electronic switch, which is controlled from the defibrillator's control module described below). The switch can be also implemented using a combination of mechanical and electronic components shown in FIG. 2 and FIG. 3.

III. A system-control and signal-conditioning feature designed to provide several functions, including:
A. Power on/off and startup diagnostic tests;
B. Minimization of the impact of defibrillator-generated EMI on the MR images described in section II ("A frontend interface panel containing connectors and adaptors") above;
C. Filtering (low-pass, band-pass, and/or adaptive filtering) of the current that the defibrillator generates for testing the electrical impedance of the contact between defibrillator pads/electrodes and the patient's skin. (We note that many commercially available defibrillators generate continuous alternating current at the frequency of approximately 60 kHz.)

Example implementations of the system-control feature include a microprocessor and/or microcontroller (e.g., MSP-430 or C2000 made by Texas Instruments, Dallas, Tex.) or a field-programmable-gate-array (FPGA; e.g., Cyclone-V made by Altera, San Jose, Calif.; Spartan-6 made by Xilinx, San Jose, Calif.).

Figure 4:
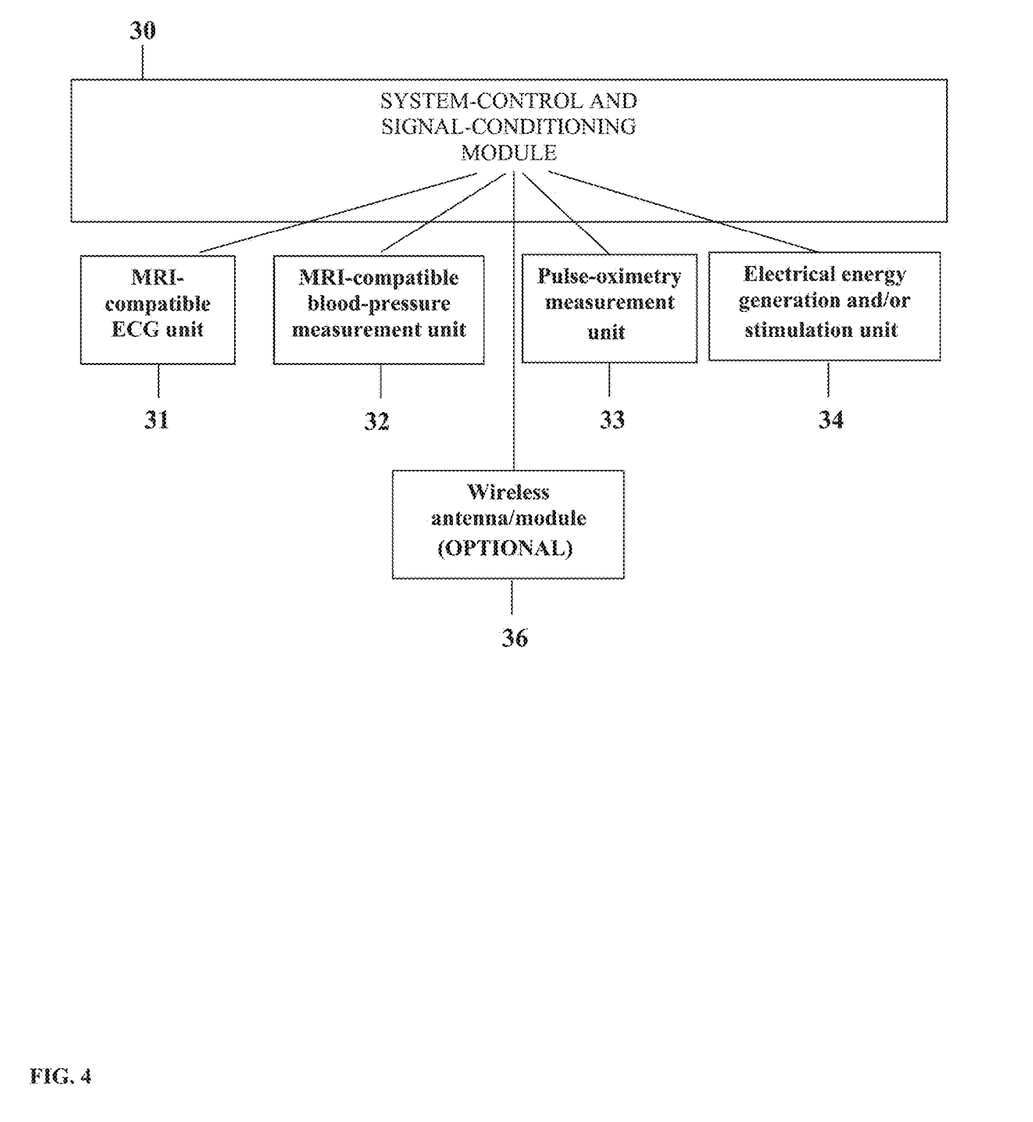
FIG. 4 is a block diagram of the system-control and signal-conditioning module (30), which may include an optional MRI-compatible ECG module (31), an optional MRI-compatible blood-pressure measurement module (32), an optional MRI-compatible module for pulse-oximetry (SpO2) measurement (33), an optional electrical energy generation and/or stimulation unit (34), and an optional wireless module/antenna (36).

The system-control and signal-conditioning feature (module 30, FIG. 4) may also include optional modules (electronic circuitry, electronic and mechanical components, firmware, and/or software) adapted to provide:
A. MRI-compatible physiological monitoring/recording, including 1- to 12-lead ECG (module 31, FIG. 4),
B. MRI-compatible blood-pressure measurement (module 32, FIG. 4), and
C. MRI-compatible pulse oximetry measurements (module 33, FIG. 4).

The MRI-compatible monitoring/recording modules may provide filtering of EMI generated by MRI scanners, including the EMI associated with gradient magnetic field (GMF) and radiofrequency (RF) interference, using the systems and methods described in Shusterman U.S. Pat. No. 9,610,016, application Ser. No. 15/442,705, and provisional application No. 62/622,996, which are incorporated herein by reference. For example, the system-control and signal-conditioning feature (30), which can be implemented using analog electronics and circuitry, digital electronic elements (e.g., the firmware installed in a microcontroller, FPGA, programmable logic device [PLD], or complex programmable logic device [CPLD], computer software), or combination thereof, include two or more of the following features:

A. One or more input sensors (e.g., ECG electrodes, coil/antenna, or a cable connection to the MRI scanner or its control unit);
B. One or more RF filters to eliminate the RF interference generated by the MRI scanner (e.g., a filter with a stop band at 64 MHz for a 1.5 T MRI scanner or at 124 MHz for a 3 T MRI scanner);
C. One or more EMI (in particular GMF) detectors, using the time-varying features of the EMI (in particular (GMF) patterns (e.g., the $1^{st}$ time derivative, the $2^{nd}$ time derivative, amplitude, time intervals between the peaks and/or time derivatives) and the differences between the features of GMF waveforms and those of physiological signals (e.g., ECG or cardiac EP signals); the GMF detector may include an edge (i.e., time-derivative) detector and/or an amplitude (level) detector, as well as a signal-averaging element, which provides an average reference level for the EMI (in particular GMF) edge and/or level detectors;
D. A short delay line (e.g., 50 microseconds) for holding the input signals to provide the time required for GMF detection described above;
E. A switch that either passes collected physiological data or stops (discards) the data containing GMF;
F. A sample-and-hold element, which keeps the most recent value before the EMI (in particular GMF) was detected and the corresponding data segment was discarded;
G. A filter for filtering remaining noise and EMI from physiological data that were passed to the filter from the previous steps; the filter characteristics may be tuned (adjusted) to eliminate the frequencies that contain GMF (or EMI) and retain physiological information, which usually contains lower frequencies than GMF (e.g., setting the low-pass filter cutoff frequency to 300 Hz would retain the ECG waveforms, whose frequency is <150 Hz, but filter out GMF, whose frequency is above 300 Hz);
H. One or more regulators for adjusting one or more parameters of the EMI (in particular GMF) detection, selected from:
1. Edge-detection threshold (time derivative) for detecting EMI (in particular GMF);
2. Level-detection threshold (amplitude) for detecting EMI (in particular GMF);
3. Dead-time regulator for adjusting one or more time intervals during which the system returns to the original state after EMI (in particular GMF) detection; this time determines the length of the data segment that is discarded after EMI (in particular GMF) detection; and
4. Regulator for adjusting one or more time intervals between two time-domain features of the EMI pattern (e.g., the EMI pattern/waveform, peak of the $1^{st}$ time derivative of the EMI waveform, peak of the $2^{nd}$ time derivative of the EMI waveform, peaks of higher derivatives of the EMI waveform).

The system-control and signal-conditioning feature (module 30, FIG. 4) may also include the following innovative features:

A. Multiple filterbanks (filtering procedures) for recording both diagnostic-quality (broad-band) signals in the absence of EMI and filtered-out (narrow-band) signals in the presence of EMI, with subsequent reconstruction of diagnostic-quality signals from the filtered-out signals using the transfer matrices (reconstruction coefficients) obtained and/or fine-tuned at the initial (calibration) stages of data recording;

B. Filtering of EMI (in particular GMF interference) using a-priori information (criteria) about differences between the GMF and physiological signals' characteristics. The criteria are adjusted using measurements performed at different distances from the magnet (i.e., at different strengths of magnetic field) in the presence and/or absence of working MR gradients;

C. Filtering of the magneto-hydrodynamic effect (MHE), using physiological measurements at different distances from the magnet (i.e., at different strengths of magnetic field) and changes in blood flow and blood pressure, which affect the magnitude of MHE;

D. One or more wireless transmitters for increasing the reliability and speed (throughput) of the wireless data transmission, which is critically important for large volumes of continuous, multichannel data.

The system-control and signal-conditioning feature (module 30, FIG. 4) may also include an optional electrical energy generation and/or stimulation unit (module 34, FIG. 4) for delivering electrical energy (waveforms) and electrical stimuli to the subject. For example, module 34 can be used to supplement or modify the defibrillation waveforms or pacing waveforms, providing:

A. Gradual ramping-up of defibrillation waveforms immediately before the defibrillation waveforms generated by the defibrillator to smooth the onset of the defibrillation waveforms; and B. Low-amplitude stimulation of skeletal muscles immediately before defibrillation to minimize patient discomfort caused by muscle contraction during defibrillation.

The system-control and signal-conditioning feature (module 30, FIG. 4) may also include a wireless antenna and/or wireless module (module 36, FIG. 4), e.g., a Bluetooth, Wi-Fi or Zigbee module, which may serve at least one of the following purposes:

A. An interface for programming data-acquisition parameters for each module (sampling rate, resolution, number of channels, duration of data acquisition, and data transmission mode [real-time transmission or recording to each module's memory card]), and B. Real-time data transmission to a data-collection and/or receiving station, e.g., a computer station for data processing, display and/or storage.

One important aspect of this invention is mounting (linking/connecting) the (optional) wireless antenna to a movable/wheeled patient table (herein, the terms patient table, bed, and procedure table are used interchangeably) to enable reliable wireless data transmission at different locations of the patient table and during its movement in the course of various procedures, as well as between different procedures and/or rooms. An important aspect of this invention is the positioning of one or more antennas connected to a wireless transmitter and one or more antennas connected to a wireless receiver (herein referred to as the first and second antenna, respectively) to provide a free (unobstructed) plane (space) for substantially continuous wireless communication between the two antennas at various positions of the patient table and during table movement.

The system of this invention, which is adapted for at least one health-related application selected from the physiological monitoring of an individual's health data, cardiac defibrillation, and pacing in the presence of EMI may further include:

one or more acquisition modules with one or more sensors adapted to be placed on an individual's skin for collecting one or more physiological signals by substantially continuous monitoring of the individual's health data, and one or more wireless transmitters for substantially continuous transmission of one or more physiological signals; and one or more wireless transmitters having one or more first antennas linked to the patient table to receive one or more physiological signals from the acquisition module and transmitting the signals substantially continuously from various locations and during movement of the patient table and the individual;

wherein one or more first antennas are positioned to provide substantially unobstructed communication to one or more second antennas on a receiver regardless of the location of the patient table and the movement of medical personnel around the table.

An important aspect of this invention is adapting digital signal processing (DSP) operations based on the properties of EMI and cardiac-activity waveforms as described below.

BRIEF DESCRIPTION OF FIGURES

A full understanding of the invention can be gained from the following description of the preferred embodiments when read in conjunction with the accompanying drawings in which:

FIG. 2 is a block diagram of a high-voltage switch implemented as a mechanical switch. The switch (25) has two states/positions: State 1: defibrillation mode, in which the defibrillator's output current is directed to the defibrillation cable; and State 2: EMI-free mode, in which the output current is redirected to an internal load (i.e., no current flows into the defibrillator cable [24]).

FIG. 3 is a block diagram of a high-voltage switch implemented as an electronic switch. The switch (25) is connected to the system-control and signal-conditioning module (30) and provides three or more states/positions: State 1: defibrillation mode, in which the defibrillator's output current is directed to the defibrillation cable (24); State 2: EMI-free mode, in which the output current is redirected to an internal load (instead of the defibrillation cable [24]); and State 3: custom mode, in which the defibrillator's output current is directed to the defibrillator cable (24) at custom time intervals/points (see Description of the Preferred Embodiments for details).

DESCRIPTION OF THE PREFERRED EMBODIMENTS

A preferred embodiment of this invention is shown in FIG. 1; it includes:
I. A nonmagnetic enclosure (100), which can be made from a nonmagnetic metal, such as bronze, brass, zinc, or aluminum, from plastic polymers, or from carbon-based materials.
II. A frontend interface (20), which provides connectors, adaptors, and switches for:
   A. Connecting input cables from an MRI-compatible hemodynamic system for monitoring pulse-oximetry (21), ECG (23), and/or blood pressure (22), which can be measured either: (i) noninvasively, using a pressure cuff or a cuff-free technique, or (ii) invasively, using a fluid-filled catheter; and
   B. Connecting output cables (e.g., defibrillation cables [24] which transmit alternating current generated by the defibrillation unit to the defibrillation electrodes/pads to test the electrical impedance of the contact between the defibrillation electrodes and the patient's skin); and
   C. Connecting (optional) filters for the input and output signals described in sections A and B above;
   D. Switching the system's operational regimes (25), using mechanical (FIG. 2) or electronic (FIG. 3) switches, or a combination of mechanical and electronic components (FIG. 2 and FIG. 3), which include:
      1. An EMI-free operating mode/regime, in which the defibrillator's current is redirected to an internal circuit/resistor located in either the frontend interface module (20) or in the system-control and signal-conditioning module (30), thereby discontinuing the current injection into the defibrillation cables, thus providing EMI-free operation. This mode is useful during diagnostic (high-quality) MR imaging.
      2. A defibrillation mode, in which the defibrillator's current is directed to the defibrillation cables and electrodes (24), thus enabling accurate estimation of the electrical impedance of the contact between the patient's skin and the defibrillator's electrodes/pads. This mode is useful when high-quality diagnostic MR imaging is not required, e.g., during real-time cardiovascular MR scanning and during MR-guided EP procedures, when external defibrillation is required.
      3. Advanced, custom-tailored modes/regimes (FIG. 3) that provide automatic switching between modes #1 and #2 above to combine the benefits of both modes and minimize EMI. For example, the mode-switching can be performed:
         a. At constant time intervals (e.g., once/minute);
         b. At time intervals that are tailored to the subject's heart rate (e.g., once in 10 heartbeats);
         c. At time intervals tailored to the subject's breathing (e.g., once in every $2^{nd}$ breathing cycle);
         d. Custom time intervals selected by a user.
III. A system-control and signal-conditioning module (30) having bidirectional communication with a defibrillator module (40) and the interface frontend (20). Module (30) provides a number of functions, including:
   i. Control of the MAGNA-DIE system and/or the external defibrillator (40), including switching the power on and off;
   ii. Control of the magnetic-field sensor (50) and activation of audio and/or visual indicator/alarm (35) when the magnetic-field strength at the system location exceeds a predefined threshold (e.g., 200 Gauss);
   iii. Adjustment (by a user) of the magnetic-field threshold for alarm activation.
IV. An external defibrillator module (40), for example, LIFEPAK 20, Physio-Control, Inc., Redmond, Wash., or an R-series defibrillator/monitor, Zoll Medical, Chelmsford, Mass.
V. A magnetic-field sensor (50), which sends magnetic-field information to module (40); for example, this sensor can be a Hall-effect sensor.
VI. A mounting/safety tool, e.g., a clamp and/or holder (60) which allows mounting/securing the system on a stable, nonmagnetic object (e.g., a pole connected to a patient table) and ensures that the system is stable and secure in the presence of EMF generated by the MRI scanner.

Figure 5:
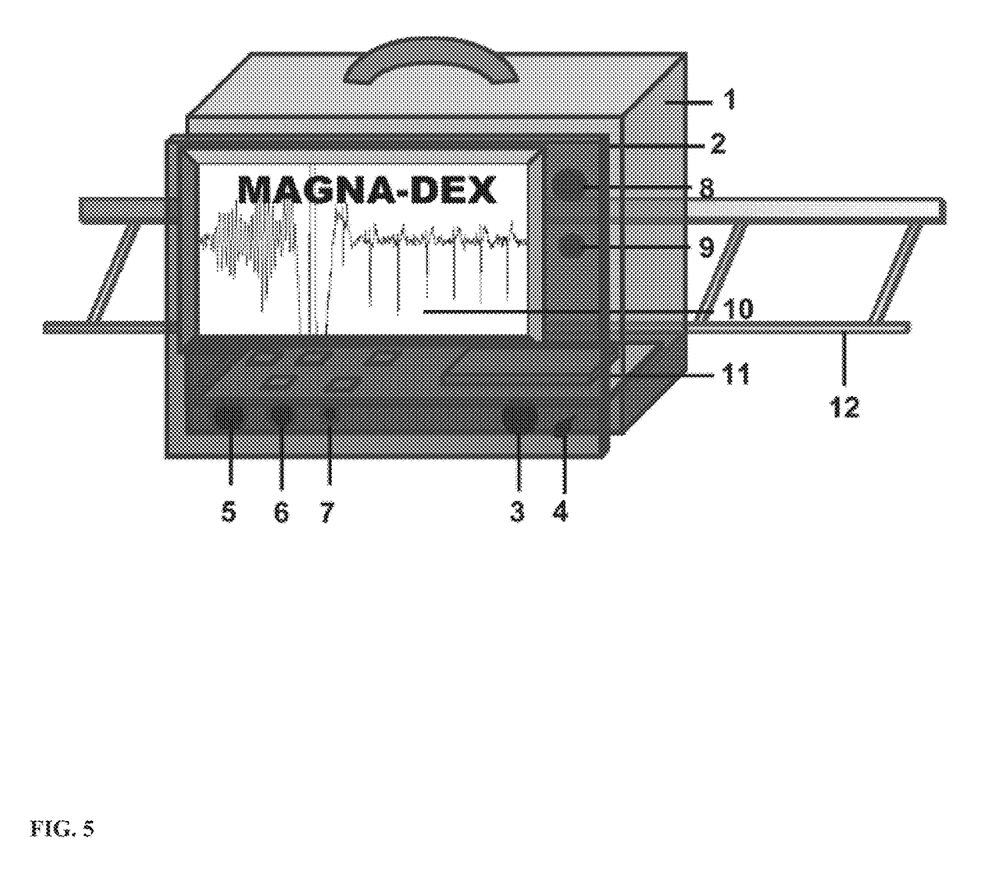
FIG. 5 is a conceptual view of the MAGNA-DEX system, which includes an enclosure (1) that houses an external defibrillation unit (e.g., LIFEPACK 20, Physio-Control Inc., Redmond, Wash., or an R-series defibrillator/monitor, Zoll Medical, Chelmsford, Mass.). The front panel (2) contains the connector for defibrillator cables (3) with the high-voltage switch (4), as well as ECG input cable connector (5) and oximetry cable connector (6). In addition, the front panel contains an input connector (7) for receiving control signals from the PELEX-MAX physiological monitoring/recording system, power ON/OFF button (8), audio-visual indicator of a strong magnetic field (9), and a transparent (plastic) door (10) for accessing the defibrillator's controls and monitoring its display. The bottom of the enclosure contains a printed circuit board (PCB) (11) with a microcontroller and other electronic components, battery, and auxiliary connectors. The unit is shown mounted on the handrail of an MR-compatible patient table (12).

A conceptual view of a preferred embodiment of the system of this invention (the MAGNA-DEX system) is shown in FIG. 5. To ensure safe deployment and MR compatibility, the example device has the following MR-safety features and MR-compatible regimes:

1) A 3D magnetic-field sensor with audio-visual indicator of a strong magnetic field. The MAGNA-DEX system has no ferromagnetic materials; only weakly magnetic and nonmagnetic materials and components are utilized. Thus, the device can be safely operated in the scanner room. It can be located, for example, at the foot of the patient table or on the scanner-room floor. Alternatively, the device can be operated remotely, by a technologist, from the control room (with the defibrillation cables threaded through the penetration panel to the scanner room).

If the device is located in the scanner room, the magnetic-field sensor ensures MR safety, activating an audio and visual (LED indicator) alarm when the magnetic-field strength exceeds a threshold (e.g., 200 Gauss in any direction), signaling that the device is located too close to the scanner bore (e.g., <1.5 m from the magnet's edge for 1.5 T scanners).

2) An EMI-free mode to enable high-quality, diagnostic MRI unimpeded by defibrillator-generated EMI. External defibrillators generate alternating current (~50-60 kHz) that flows through the defibrillation cable and electrodes in order to determine skin-electrode impedance (i.e., the electrical impedance between the defibrillator electrode/pad and the skin of a subject, or the electrode-skin contact) and calculate the appropriate defibrillation energy. Unfortunately, the alternating current (herein referred to as the impedance-testing electrical current) generates significant EMI in MR images. To address this problem, the system can be switched to an EMI-free mode, in which the alternating current is redirected to an internal load so that no current flows through the defibrillation cables. (Note that the device provides continuous ECG and SpO2 monitoring, as well as other control functions in this mode.) The EMI-free mode is implemented using a high-voltage switch (FIG. 5, switch 4); it is activated using one of the following options:

A. Manual switching;
   B. Asynchronous switching at constant duty cycle without synchronization with the scanner's operation;
   C. Synchronous switching, synchronized with the scanner operation using, e.g., the control signal received from PinMed's PELEX-MAX hemodynamic monitoring and recording system, which has the capability to detect magnetic-field gradients and to send this information in real time to the MAGNA-DEX system (FIG. 5, connector 7).
   D. Advanced synchronization options, providing customized synchronization for various MRI pulse sequences.

3) MR safety of the cables and electrodes is achieved by utilizing high-voltage, low-impedance cables, as well as commercially available radiolucent defibrillation electrodes (e.g., Quik-Combo, Physio-Control, Redmond, Wash.).

4) MR safety of the power supply. To ensure MR safety, the MAGNA-DEX unit can be powered by a nonmagnetic, rechargeable battery.

5) MR safety of the main (control) unit is ensured by using: a) defibrillators that contain only weakly magnetic materials; and b) using the magnetic-field sensor and audio-visual alarm to ensure that the magnetic field at the unit location is less than a preset threshold (e.g., 200 Gauss).

6) A PCB with a microcontroller (MCU). The MCU can be programmed to control the system operation and to provide advanced synchronization with the scanner's operation, thus improving system usability and reducing EMI, as described above.

7) Mounting tool (e.g., clamp(s) and/or holder(s)). This additional safety feature provides extra protection against the magnetic attraction force generated by MR scanners. The mounting tool can be affixed to the rear wall of the enclosure to allow the unit's mounting on immovable or securely fixed-in-place nonmagnetic structures, such as the handrails (FIG. 5) of an MR-compatible patient table, nonmagnetic intravenous-injection (IV) poles attached to a patient table, and other horizontal or vertical structures. Alternatively, the mounting tool can be used for strapping the unit to an immovable object.

EXAMPLES

Example 1. An MRI-Guided EP Study

This hypothetical example describes the application of a medical device of this invention for safe and efficient external cardiac defibrillation during an MRI-guided EP study.

The MAGNA-DEX device of this invention would be brought into the scanner room and initially positioned 25 cm from the edge of an MRI magnet bore, which would trigger an audio-visual alarm indicating a strong EMF that exceeds the preset threshold of 200 Gauss. The MAGNA-DEX device would then be moved away from the magnet and affixed to the end of a patient table located approximately 1.5 m from the MRI magnet bore.

Because many defibrillator functions require continuous, high-quality ECG, blood pressure, or pulse-oximetry signals, which may become obscured by the high-level EMI generated by MRI scanners (especially during real-time cardiovascular imaging, which requires the application of steady-state-free-precession pulse sequences with very short duty cycle, time to repeat, and time to echo), the input connectors of the MAGNA-DEX system would be connected to the ECG, arterial-pressure, and/or pulse-oximetry cables from an MRI-compatible hemodynamic monitoring system (TELEX-MAX), which provides continuous, high-quality hemodynamic monitoring even during real-time MRI scanning.

The procedure usually involves high-quality diagnostic imaging, during which the MAGNA-DEX system would be switched to the EMI-free mode to minimize the EMI generated by the defibrillator.

Subsequently, the MAGNA-DEX system would be switched to the defibrillation mode when the physicians performing the procedure started cardiac EP mapping, which is frequently associated with the induction of life-threatening cardiac arrhythmias. If ventricular fibrillation occurred, the MAGNA-DEX system would be used to defibrillate the patient safely inside the magnet bore.

If the clinicians needed to apply synchronized (on-demand) pacing, the MAGNA-DEX system would use the hemodynamic monitoring signals (ECG, blood pressure, and/or oximetry) received from an MRI-compatible monitoring system to provide synchronized (on-demand) pacing, in which the pacing is inhibited during intrinsic ECG activity.

If the clinicians needed to apply synchronized cardioversion, the MAGNA-DEX system would use the hemodynamic monitoring signals (ECG, blood pressure, and/or oximetry) received from an MRI-compatible monitoring system to synchronize cardioversion with intrinsic ECG activity and to provide electrical discharge at the specific time delay relative to the QRS complex on the ECG.

Whereas particular aspects of the method of the present invention and particular embodiments of the invention have been described for purposes of illustration, it will be appreciated by those skilled in the art that numerous variations of the details may be made without departing from the invention as described in the appended claims.

The invention claimed is:

1. A system adapted for performing at least one operation selected from external cardiac defibrillation, cardiac pacing, and physiological monitoring in an MRI environment, said system comprising:
   a substantially nonmagnetic enclosure;
   at least one sensor adapted for collecting at least one signal containing physiological data from the body of a subject;
   an interface module in said nonmagnetic enclosure containing at least one EMI detector based on at least one time-domain feature having a different range of values for EMI compared with the range of values of said time-domain feature for said physiological data, to identify EMI within said at least one signal;
   at least one processing element for minimizing said EMI within the time intervals in which said EMI is detected;
   at least one adapter for connecting said body of a subject to at least one device selected from a defibrillator, a cardiac pacing device, and a monitoring device; and
   at least one switch adapted for switching of the direction of the impedance-testing electrical current between at least two modes of operation selected from: (i) an EMI-free regime, in which said electrical current is redirected to an internal load; and (ii) a defibrillation regime, in which said electrical current is redirected to the defibrillation cable.

2. A system as set forth in claim 1, in which said at least one sensor is selected from: 1) a sensor of external magnetic-field strength, 2) an alarm activated in the presence of an external magnetic-field strength that exceeds a preset threshold, and 3) an ECG sensor, an electromyographic (EMG) sensor, an electroencephalographic (EEG) sensor, a blood-pressure sensor, a pulse-oximetry sensor, and an accelerometer sensor.

3. A system as set forth in claim 1, which further includes at least one system-control and signal-conditioning module, wherein said module contains at least one unit selected from an MRI-compatible ECG unit, an MRI-compatible blood-pressure measurement unit, an MRI-compatible unit for pulse-oximetry (SpO2) measurement, and an electrical energy generation and/or stimulation unit.

4. A system as set forth in claim 1 in which said at least one EMI detector is selected from an edge detector, a level detector, a peak amplitude detector, a peak $1^{st}$ time derivative detector, a peak $2^{nd}$ time derivative detector, a detector for measuring the time interval between the peak EMI amplitude and at least one time derivative, and a detector for measuring the time interval between the peak $1^{st}$ derivative and the peak $2^{nd}$ derivative.

5. A system as set forth in claim 1 in which said at least one processing element for minimizing said EMI performs at least one operation selected from complete EMI blanking, partial EMI blanking, EMI clipping, EMI attenuation, and EMI filtering.

6. A system as set forth in claim 1 which includes at least one wireless transmitter for transmitting said physiological data and at least one wireless receiving station for receiving said physiological data from said at least one wireless transmitter.

7. A system as set forth in claim 1 which includes at least one device selected from defibrillator, cardiac pacing device and monitoring device in said nonmagnetic enclosure.

8. A system as set forth in claim 1 in which said interface module includes at least one mode of switching of the direction of the impedance-testing electrical current, wherein said switching is selected from: (i) manual switching; (ii) switching at constant time intervals; (iii) switching at time intervals that are tailored to the heart rate of a subject; (iv) switching at time intervals tailored to the breathing movements of a subject; (v) switching at time intervals synchronized with the MRI scanner operation; and (vi) switching at custom time intervals selected by a user.

9. A system as set forth in claim 1 wherein said at least one processing element is selected from:
   a. at least one delay line for holding said at least one signal during the time required for EMI detection;
   b. at least one switch for performing at least two operations on the output signal from said at least one EMI detector, wherein said operations are selected from:
      i. passing said output signal from said at least one EMI detector to at least one data-acquisition element during the time intervals in which no EMI is detected; and
      ii. discarding said output signal during the time intervals in which EMI is detected;
   c. at least one element for regulating the switching-on delay of said at least one switch after EMI is detected, which determines the duration of the discarded segment of said at least one signal during EMI periods;
   d. at least one sample-and-hold element for holding the last value of said at least one signal preceding the time interval in which said EMI is detected; and
   e. at least one filter element selected from:
      i. an RF filter respecting the Larmor frequency of the magnetic-field source generating said EMI; and
      ii. a low-pass filter respecting the difference between the frequency of said EMI and said physiological data for filtering residual noise and EMI from said at least one signal.

10. A system as set forth in claim 9 in which said at least one EMI detector is selected from an edge detector, a level detector, a peak amplitude detector, a peak $1^{st}$ time derivative detector, a peak $2^{nd}$ time derivative detector, a detector for measuring the time interval between the peak EMI amplitude and at least one time derivative, and a detector for measuring the time interval between the peak $1^{st}$ derivative and the peak $2^{nd}$ derivative.

11. A system as set forth in claim 9 in which said at least one processing element for minimizing said EMI performs at least one operation selected from complete EMI blanking, partial EMI blanking, EMI clipping, EMI attenuation, and EMI filtering.

12. A system as set forth in claim 9 in which said at least one sensor is selected from an ECG sensor, an EMG sensor, an EEG sensor, a blood-pressure sensor, a pulse-oximetry sensor, and an accelerometer sensor.

13. A system adapted for at least one health-related application selected from the physiological monitoring of a subject's health data, cardiac defibrillation, and pacing in the presence of EMI generated by an MRI scanner during an MRI scan of said subject, said system comprising:

a substantially nonmagnetic enclosure;
at least one sensor adapted for collecting at least one signal containing physiological data from the body of said subject;
at least one adapter for connecting said body of a subject to at least one device selected from a defibrillator, a cardiac pacing device, and a monitoring device;
an interface module in said nonmagnetic enclosure containing at least one EMI detector based on at least one time-domain feature having a different range of values for EMI compared with the range of values of said time-domain feature for said physiological data, to identify EMI within said at least one signal; and
at least one processing element for minimizing said EMI within the time intervals in which said EMI is detected;
wherein said at least one processing element includes at least one element selected from:
a. at least one delay line for holding said at least one signal during the time required for EMI detection;
b. at least one switch for performing at least two operations on the output signal from said at least one EMI detector, wherein said operations are selected from:
  i. passing said output signal from said at least one EMI detector to at least one data-acquisition element during the time intervals in which no EMI is detected; and
  ii. discarding said output signal during the time intervals in which EMI is detected;
c. at least one element for regulating the switching-on delay of said at least one switch after EMI is detected, which determines the duration of the discarded segment of said at least one signal during EMI periods;
d. at least one sample-and-hold element for holding the last value of said at least one signal preceding the time interval in which said EMI is detected; and
e. at least one filter element selected from:
  i. an RF filter respecting the Larmor frequency of the magnetic-field source generating said EMI; and
  ii. a low-pass filter respecting the difference between the frequency of said EMI and said physiological data for filtering residual noise and EMI from said at least one signal.

14. A system as set forth in claim 13 in which said at least one EMI detector is selected from an edge detector, a level detector, a peak amplitude detector, a peak $1^{st}$ time derivative detector, a peak $2^{nd}$ time derivative detector, a detector for measuring the time interval between the peak EMI amplitude and at least one time derivative, and a detector for measuring the time interval between the peak $1^{st}$ derivative and the peak $2^{nd}$ derivative.

15. A system as set forth in claim 13 in which said at least one processing element for minimizing said EMI performs at least one operation selected from: complete EMI blanking, partial EMI blanking, EMI clipping, EMI attenuation, and EMI filtering.

16. A system as set forth in claim 13 in which said at least one sensor is selected from an ECG sensor, an EMG sensor, an EEG sensor, a blood-pressure sensor, a pulse-oximetry sensor, and an accelerometer sensor.

17. A system adapted for performing at least one operation selected from external cardiac defibrillation, cardiac pacing, and physiological monitoring in an MRI environment, said system comprising:
a substantially nonmagnetic enclosure;
at least one sensor adapted for collecting at least one signal containing physiological data from the body of a subject;
an interface module containing at least one EMI detector based on at least one time-domain feature having a different range of values for EMI compared with the range of values of said time-domain feature for said physiological data, to identify EMI within said at least one signal; and
at least one processing element for minimizing said EMI within the time intervals in which said EMI is detected;
wherein said at least one processing element is selected from:
a. at least one delay line for holding said at least one signal during the time required for EMI detection;
b. at least one switch for performing at least two operations on the output signal from said at least one EMI detector, wherein said operations are selected from:
  i. passing said output signal from said at least one EMI detector to at least one data-acquisition element during the time intervals in which no EMI is detected; and
  ii. discarding said output signal during the time intervals in which EMI is detected;
c. at least one element for regulating the switching-on delay of said at least one switch after EMI is detected, which determines the duration of the discarded segment of said at least one signal during EMI periods;
d. at least one sample-and-hold element for holding the last value of said at least one signal preceding the time interval in which said EMI is detected; and
e. at least one filter element selected from:
  i. an RF filter respecting the Larmor frequency of the magnetic-field source generating said EMI; and
  ii. a low-pass filter respecting the difference between the frequency of said EMI and said physiological data for filtering residual noise and EMI from said at least one signal.

18. A system as set forth in claim 17 in which said at least one processing element for minimizing said EMI performs at least one operation selected from complete EMI blanking, partial EMI blanking, EMI clipping, EMI attenuation, and EMI filtering.

19. A system as set forth in claim 17 in which said at least one sensor is selected from an ECG sensor, an EMG sensor, an EEG sensor, a blood-pressure sensor, a pulse-oximetry sensor, and an accelerometer sensor.

20. A system as set forth in claim 17 in which said at least one EMI detector is selected from an edge detector, a level detector, a peak amplitude detector, a peak $1^{st}$ time derivative detector, a peak $2^{nd}$ time derivative detector, a detector for measuring the time interval between the peak EMI amplitude and at least one time derivative, and a detector for measuring the time interval between the peak $1^{st}$ derivative and the peak $2^{nd}$ derivative.

* * * * *